United States Patent
Varn

Patent Number: 5,362,305
Date of Patent: Nov. 8, 1994

[54] HIP AND KNEE ABDUCTOR

[75] Inventor: Harold T. Varn, Lawrenceville, Ga.

[73] Assignee: Restorative Care of America Incorporated, Clearwater, Fla.

[21] Appl. No.: 15,604

[22] Filed: Feb. 9, 1993

[51] Int. Cl.⁵ .................................. A61F 5/00
[52] U.S. Cl. .................................. 602/24; 602/23; 128/882
[58] Field of Search ............... 602/5, 23–25; 128/869, 878, 882

[56] References Cited

U.S. PATENT DOCUMENTS

| | | | |
|---|---|---|---|
| 1,635,638 | 7/1927 | Rogers | 128/882 |
| 2,815,021 | 12/1957 | Freeman | 602/24 |
| 3,815,589 | 6/1974 | Bosley | 602/24 |
| 4,046,143 | 9/1977 | Bell. | |
| 4,071,023 | 1/1978 | Gregory. | |
| 4,543,948 | 10/1985 | Phillips et al. | 602/24 X |
| 4,747,779 | 5/1988 | Gerstung. | |
| 4,881,532 | 11/1989 | Borig et al. | 602/24 X |

FOREIGN PATENT DOCUMENTS

| | | | |
|---|---|---|---|
| 0741872 | 6/1980 | U.S.S.R. | 602/24 |
| 1147393 | 3/1985 | U.S.S.R. | 602/24 |

OTHER PUBLICATIONS

Richards Orthopedic Catalog, 1981, pp. 70.1 and 76.
"Richards Pehr Abduction Hip Splint" Advertisement; Journal of Bone & Joint Surgery, Mar. 1965, vol. 47-A #2, p. 81.

*Primary Examiner*—Stephen R. Crow
*Assistant Examiner*—Linda C. M. Dvorak
*Attorney, Agent, or Firm*—Zarley, McKee, Thomte, Voorhees & Sease

[57] ABSTRACT

The hip and knee abductor device of the present invention includes a pair of C-shaped thigh cuffs that engage the inner thigh of a patient at a location above the knee. A telescoping spacer bar is pivotally connected at opposite ends to each of the cuffs so that the degree of hip abduction is selectively controlled. A strap is provided on each cuff for securing the cuff to the patient's leg. The cuffs can be changed from a static position wherein there is no relative movement between the cuffs to a reciprocating function wherein the cuffs can move forwardly and rearwardly relative to one another, thereby allowing ambulation by the patient.

18 Claims, 2 Drawing Sheets

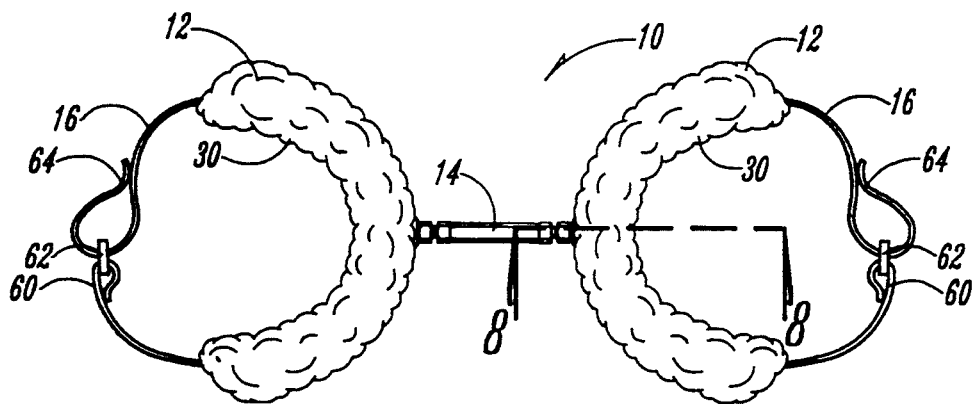
FIG.4
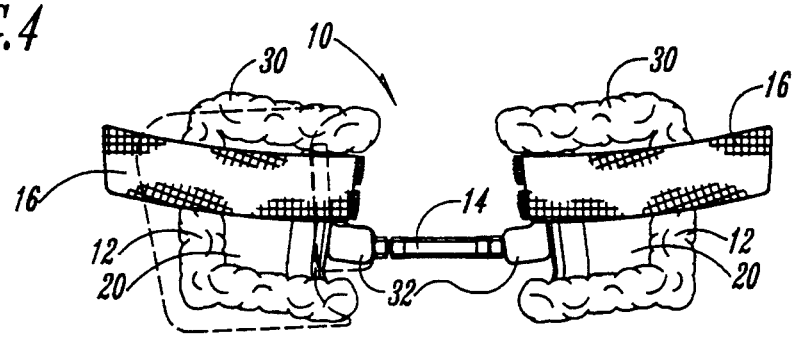
FIG.7
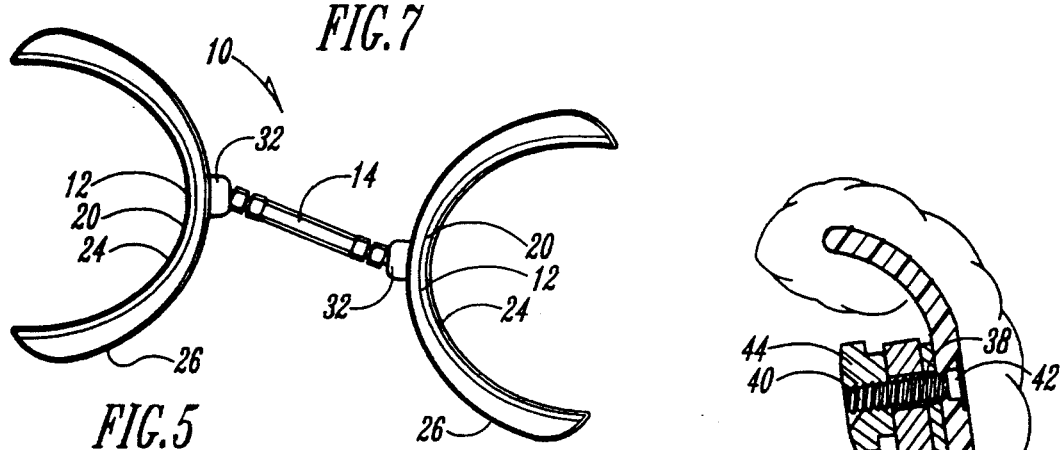
FIG.5
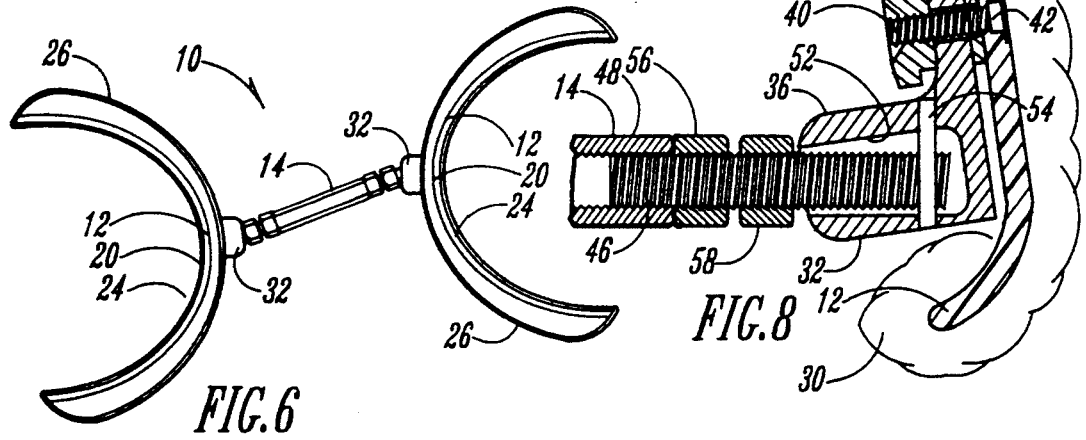
FIG.6
FIG.8

HIP AND KNEE ABDUCTOR

BACKGROUND OF THE INVENTION

It is desirable for patients who have had hip surgery to control the degree of hip abduction. Control of hip abduction is also necessary for correction of some types of congenital hip defects and hip dislocations, such as Legg Perthes. Also, use of devices to control scissoring of tight abductor muscles of the legs is also necessary treatment for some patients. In the prior art, devices have been used for controlling abduction and scissoring of the legs, such as wedge-shaped pillows and rigid braces. However, such prior art devices have not been adjustable to accommodate varying degrees of abduction, nor have such devices allowed for ambulation or reciprocal gait training of the patient.

Therefore, a primary objective of the present invention is the provision of an improved hip and knee abductor device.

Another objective of the present invention is the provision of a hip and knee abductor device which is adjustable to accommodate varying degrees of abduction.

A further objective of the present invention is the provision of a hip and knee abductor device which allows for patient ambulation.

Still another objective of the present invention is the provision of a hip and knee abductor device which controls scissoring of the patient's legs.

A further objective of the present invention is the provision of a hip and knee abductor device which is quick and easy to place on the patient, comfortable to wear, durable in use, and economical to manufacture.

These and other objectives will become apparent from the following description of the invention.

SUMMARY OF THE INVENTION

The hip and knee abductor device of the present invention includes a pair of opposing C-shaped cuffs adapted to engage the inner thigh of the patient above the knee. A spacer bar has opposite ends which are pivotally connected to each of the cuffs. The spacer bar includes a turnbuckle such that the length of the bar is adjustable, thereby allowing for a selective degree of abduction. The cuffs are substantially rigid and covered with a fleece-like material so as to be comfortable to the patient wearing the device. An adjustable strap is attached to each cuff and extends around the patient's leg so that each cuff can be secured to the patient's thigh. The cuffs are movable between a static position wherein relative movement between the cuffs is prevented, and a reciprocating position which allows the cuffs to move forwardly and rearwardly relative to one another so that the patient may walk or ambulate while wearing the device.

BRIEF DESCRIPTION OF THE DRAWINGS

FIG. 4 is a bottom plan view of the device in a static position.

FIGS. 5 and 6 are views similar to FIG. 4 showing the relative forward and rearward movement of the cuffs in a reciprocating position.

FIG. 7 is a side elevation view of the device.

FIG. 8 is a sectional view taken along lines 8—8 of FIG. 4.

DETAILED DESCRIPTION OF THE PREFERRED EMBODIMENT

Figure 1:
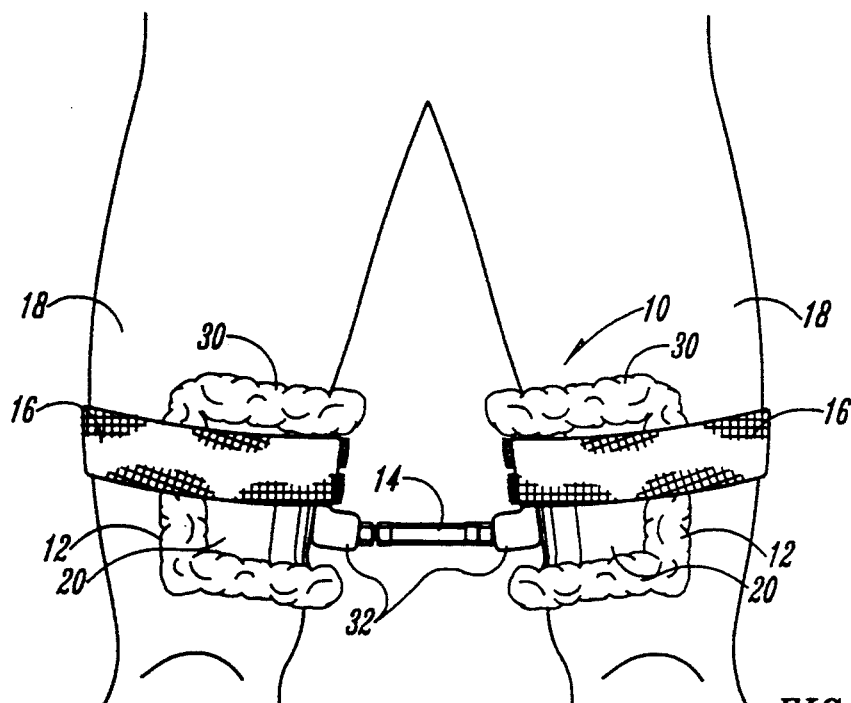
FIG. 1 is a side elevation view of the hip and knee abductor device of the present invention as worn by a patient.
Figure 2:
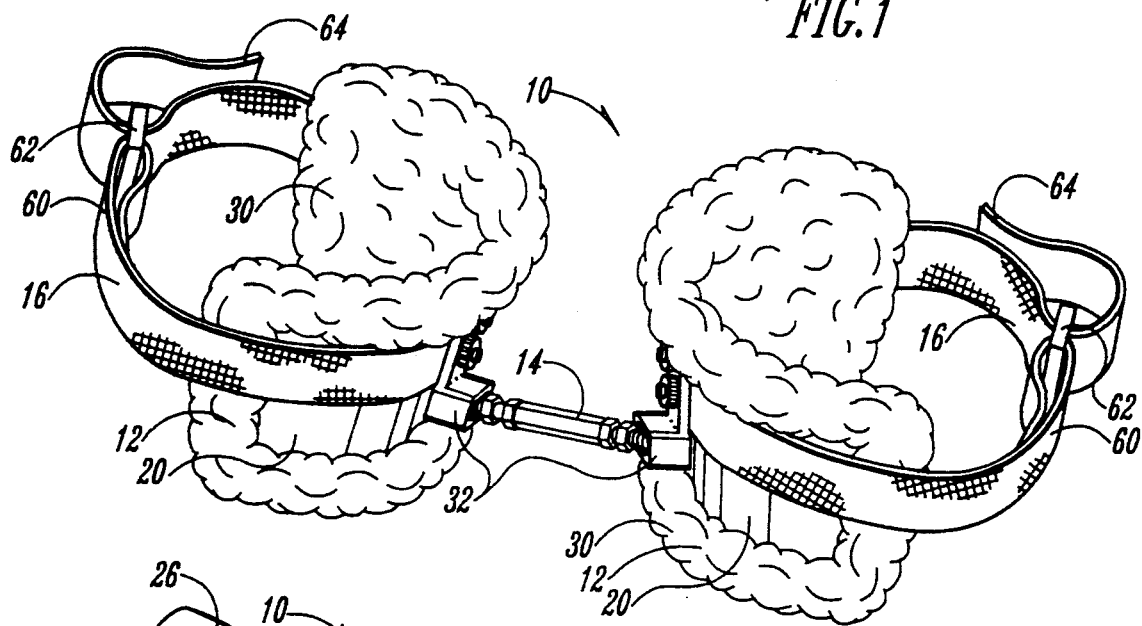
FIG. 2 is a perspective view of the device.
Figure 3:
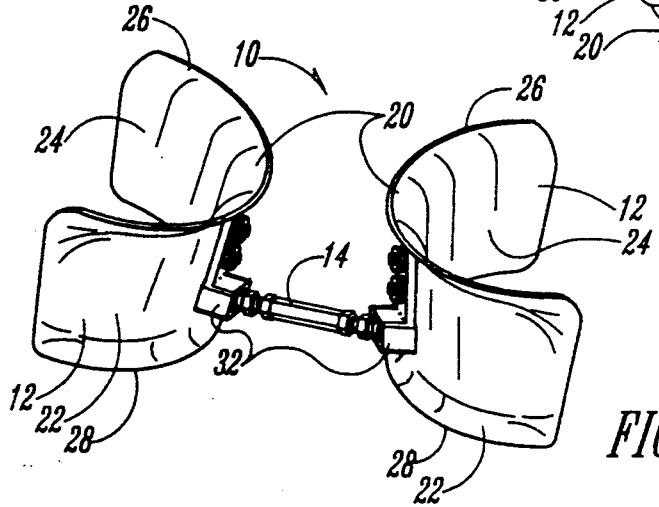
FIG. 3 is a perspective view of the cuffs of the device, with the securing straps and fleece padding removed therefrom.

The hip and knee abductor device of the present invention is generally designated by the reference numeral 10 in the drawings. The device includes a pair of C-shaped cuffs 12, a spacer bar 14 interconnecting the cuffs 12, arid a strap 16 on each cuff 12 for securing the cuff to a patient's leg 18, as shown in FIG. 1. The cuffs engage the inner thigh of the patient at a position above the knee so as to control hip and knee abduction, and so as to control scissoring of tight abductor muscles in the legs. Each cuff 12 includes a rigid member 20 having an inner surface 22 and an outer surface 24. Each rigid cuff member 20 also has an outwardly curved upper edge 26 and an outwardly curved lower edge 28, as seen in FIG. 3. Each cuff member 20 is at least partially covered with a soft fleece-like padding material 30 along the outer surface 24 and the upper and lower edges 26, 28 so as to be comfortable and to prevent abrasion. Preferably, the material 30 is Kodel ®.

Each cuff 12 includes a bracket 32 mounted on the inner surface 22 of the rigid member 20. Each bracket 32 includes an upper flange 34 and a lower socket 36. The flange 34 is connected to the rigid member 20 of the respective cuff 12 with bolt-like fasteners 38, as best seen in FIG. 8. The fasteners 38 each include a threaded shaft 40 extending through the rigid member 20 and through the flange 34 of the bracket 32. The outer end of the shaft 40 includes a head 42 which is preferably mounted within a recess in the rigid member 20 such that the head 42 is flush with the outer surface 24 of the member 20. A knurled nut 44 is threadable onto the shaft 40, and can be finger tightened thereon so as to secure the bracket 32 to the rigid cuff member 20. Preferably, two fasteners 38 are used for each of the brackets 32, so as to prevent pivotal movement of the bracket relative to the rigid cuff member 20.

The spacer bar 14 includes a pair of threaded shafts 46 with a turnbuckle 48 threadably interconnecting the two shafts 46. The ends 50 of the shafts 46 are received within an elongated slot 52 in the respective socket 36, and pivotally secured therein by a pin 54, as best seen in FIG. 8. As seen in FIG. 8, the pin 54 is offset at an angle with respect to a principle plane defined by the flange 34 of the bracket 32. Since the socket 36 is located below the midpoint of the cuff 12, the upper edge 26 of the cuff 12 is angled inwardly, as seen in FIGS. 1 and 8. The pin 54 allows pivotal movement between each cuff 12 and the turnbuckle 48 about the Longitudinal axis of the pin. Also, there is sufficient play between the end 50 of the shaft 46 and the pin 54 so as to allow the cuff 12 to pivot about a substantially horizontal plane, as indicated by dotted lines in FIG. 7 . Thus, the cuffs 12 are pivotal toward and away from one another to accommodate different shaped legs of different patients. Other types of universal joints may be used as a connector between the bar 14 and the cuffs 12.

The shafts 46 are mirror images of one another, such that the threads thereon are disposed in opposing angular directions Accordingly, rotation of the turnbuckle 48 in one direction about its longitudinal axis draws the shafts 46 into the turnbuckle 48, thereby decreasing the spacing between the cuffs 12. Similarly, rotating the turnbuckle about its longitudinal axis in the opposite direction extends the shafts 46 outwardly from the turnbuckle, thereby increasing the space between the cuffs 12. Thus, the space between the cuffs is adjustable to accommodate different desired degrees of abduction. The turnbuckle 48 can be replaced with longer or shorter similar turnbuckles, so as to provide greater variance in the degree of abduction permitted by the device 10. Preferably, the range of abduction is between 20°-60°. A lock nut 56 is provided on each of the shafts 46 so as to prevent rotation of the turnbuckle 48 after the desired spacing between the cuffs 12 has been set. Turning the nuts 56 into engagement with the ends of the turnbuckle 48 prevent the turnbuckle from being turned in a direction to decrease the spacing between the cuffs.

A second lock nut 58 is provided on each of the shafts 46 so as to control the pivotal movement of the cuffs 12 about the axis of the pin 54. When the lock nut 58 is threaded into engagement with the socket 36, as shown in FIG. 4, the cuffs are in a static, non-pivotal position which does not allow forward and rearward movement of the cuffs relative to one another. When the lock nuts 56 are threaded out of engagement with the respective socket 36, as shown in FIGS. 5 and 6, the device 10 is in a reciprocating function wherein the cuffs 12 can move forwardly and rearwardly with respect to one another. The fore and aft movement of the cuffs is permitted by the slot 52 in each of the sockets 36. The degree of relative movement between the cuffs 12 when the device 10 is in the reciprocating function can be adjusted by moving the lock nuts 58 closer to or farther away from the sockets 36. As the lock nut 58 is moved closer to the socket 36, the movement of the shaft 40 within the slot 52 of the socket 36 becomes more limited by the physical contact between the lock nut 58 and the socket 30. Similarly, movement of the nut 58 away from the socket 36 allows for increased movement the shaft 40 within the slot 52.

Each securing strap 16 extends between the bracket 32 and the rigid cuff member 20, so as to be sandwiched therebetween, as seen in FIG. 8. Thus, the straps 16 are secured to the cuffs 12. Each strap 16 includes a first end 60 having a ring 62 fixed thereto. The second end 64 of the strap 10 extends through the ring 62 so that the strap doubles over upon itself. Preferably, at least the second end 64 of the strap is made of a VELCRO® loop and hook material so that the second end 64 adheres to itself.

In use, the degree of abduction is first set by adjusting the telescoping spacer bar 14. Such adjustment is accomplished by rotating the turnbuckle 48 in one direction to increase the spacing between the cuffs, and in the opposite direction to decrease the spacing between the cuffs. The lock nuts 56 are then tightened against the ends of the turnbuckle. The degree of relative movement between the cuffs is also adjusted, from a static position with no relative movement between the cuffs and a reciprocating position allowing forward and rearward relative movement of the cuffs. This movement between the static and the reciprocating functions of the device 10 is controlled by the nuts 58. After passively stretching the patient's thigh abductors, the orthosis device 10 can be positioned on the inner aspect of the thighs above the knee of the patient. The spacer bar 14 should be located near the knees so as to achieve a wider space between the knees than at mid-thigh, as seen in FIG. 1. The straps 16 can be secured around the patient's leg so as to be snug, but not overly tight. The straps should be sufficiently tight to prevent migration of the orthosis on the legs.

The knee and hip orthosis device of the present invention aids patients that have decreased physical mobility related to impaired neuromuscular or muscular skeletal function resulting from hip surgery, congenital defects, or other problems. The device controls hip abduction and leg scissoring. With the device 10, the patient is able to maintain or regain maximal neuromuscular function of the affected limb and prevents permanent deformity. The device can be used in a static manner so as to prevent any relative movement of the patient's legs, and can be used in a reciprocating manner for gait training of the patient. The device 10 can be worn by a patient in bed or in a wheelchair.

The invention has been shown and described above in connection with the preferred embodiment, and it is understood that many modifications, substitutions and additions may be made which are within the intended broad scope of the invention. From the foregoing, it can be seen that the present invention accomplishes at least all of the stated objectives.

What is claimed is:

1. A hip and knee abductor device comprising:
 a pair of C-shaped cuffs adapted to engage the inner thigh of a patient above the knee;
 a single length-adjustable spacer bar extending between the cuffs so as to maintain the patient's legs in a selectively spaced apart orientation;
 strap means for securing the cuffs to the patient's legs; and mounting means for pivotally mounting the spacer bar to each cuff, such that each cuff is adapted to be rotated about a single axis substantially parallel to the patient's legs thereby allowing patient ambulation.

2. The device of claim 1 wherein the spacer bar has opposite ends and the mounting means includes a pair of pins operatively attached to respective cuffs and extending through respective ends of the spacer bar, each pin defining an axis about which the respective cuff is pivotal.

3. The device of claim 1 wherein the spacer bar includes a turnbuckle which is rotatable in one direction for increasing the length of the bar and which is rotatable in an opposite direction for decreasing the length of the bar.

4. The device of claim 3 further comprising releasable lock means for selectively moving the cuffs into a static position and a reciprocating position.

5. The device of claim 1 wherein the cuffs each include a rigid member to which the spacer bar is attached, and padding partially covering the rigid member for engaging the patient's leg.

6. The device of claim 1 wherein the cuffs are angularly disposed toward one another so as to provide 20°-60° of abduction.

7. An orthosis device for controlling abduction of a patient's legs and for allowing ambulation by the patient, the device comprising: z
 a first cuff adapted to engage an inside portion of a patient's left leg;
 a second cuff adapted to engage an inside portion of the patient's right leg;
 a single rigid bar pivotally connected at opposite ends to the first and second cuffs to allow the cuffs to move relative to one another about an axis substantially parallel to the patient's legs; and securement means for securing the cuffs to the patient's legs.

8. The device of claim 7 further comprising a pair of mounting brackets, one bracket being secured to each cuff, each bracket including a pin extending through the bar such that the bar is pivotal about the axis of the pin.

9. The device of claim 8 further comprising lock means for preventing pivotal movement of the bar.

10. The device of claim 7 further comprising mounting means providing a universal joint between the cuffs and the bar.

11. The device of claim 7 wherein the bar is telescoping so as to have a selectively adjustable length.

12. The device of claim 7 wherein the bar includes a turnbuckle which is rotatable in opposite directions to increase and decrease the spacing between the cuffs.

13. The device of claim 7 further comprising padding means at least partially covering the cuffs to prevent abrasion on the patient's legs.

14. The device of claim 7 wherein the bar interconnects the cuffs such that the cuffs are angularly disposed with respect to one another.

15. A method of controlling hip abduction and leg scissoring in a patient, the method comprising:

adjusting the spacing between a pair of interconnected thigh cuffs with a single adjustable spacer bar, each cuff being adapted for pivotal movement about a single axis substantially parallel to the patient's legs to permit patient ambulation; and securing the cuffs to the patient's legs.

16. The method of claim 15 further comprising tightening a lock nut to fix the spacing between the cuffs.

17. The method of claim 15 further comprising selecting a degree of pivotal movement between the cuffs.

18. The method of claim 15 further comprising selectively setting the cuffs between a static position wherein relative forward and rearward movement between the cuffs is substantially eliminated and a reciprocating position wherein the cuffs are movable forwardly and rearwardly relative to one another.

* * * * *